United States Patent [19]

Ansuini et al.

[11] Patent Number: 4,957,616
[45] Date of Patent: Sep. 18, 1990

[54] TUBE SHEET WITH REFERENCE ELECTRODE

[75] Inventors: Frank Ansuini, Lincoln, R.I.; Paul Fulford, Jupiter, Fla.

[73] Assignee: Electrochemical Devices, Inc., Albion, R.I.

[21] Appl. No.: 453,131

[22] Filed: Dec. 12, 1989

Related U.S. Application Data

[63] Continuation of Ser. No. 277,490, Nov. 29, 1988, abandoned, which is a continuation of Ser. No. 30,876, Mar. 26, 1987, abandoned.

[51] Int. Cl.$^5$ .................. G01M 27/30; C23F 13/00; F28F 19/00
[52] U.S. Cl. .................. 204/435; 204/196; 165/134.1
[58] Field of Search ............. 204/435, 147, 196, 148, 204/197; 165/134.1

[56] References Cited

U.S. PATENT DOCUMENTS

| | | | |
|---|---|---|---|
| 1,779,232 | 10/1930 | Handforth | 204/435 |
| 2,338,713 | 1/1944 | Ewing | 204/435 |
| 2,846,385 | 8/1958 | Buchan | 204/197 |
| 2,910,420 | 10/1959 | Preiser | 204/435 |
| 3,202,596 | 8/1965 | Canevari | 204/197 |
| 3,378,472 | 4/1968 | Banks et al. | 204/196 |
| 3,438,875 | 4/1969 | Watanabe et al. | 204/435 |
| 3,625,851 | 12/1971 | Geld | 204/196 |
| 4,273,637 | 6/1981 | MacDonald | 204/435 |
| 4,636,292 | 1/1987 | Fejes et al. | 204/435 |

OTHER PUBLICATIONS

Simon, "Tube Sheet Corrosion and Mitigation Techniques in Seawater Cooled Titanium-Aluminum Bronze Condenser", Apr. 1983, pp. 77/1-77/9.
Beavers et al., "Corrosion Related Failures in Power Plant Condensers", Oct. 1981, pp. 19-26.
Nickel Topics, "Experiences with Stainless Steel Tubes in Utility Condensers", p. 5.

*Primary Examiner*—T. Tung
*Attorney, Agent, or Firm*—Lorusso & Loud

[57] ABSTRACT

A tube sheet with an attached reference electrode is provided for use in heat exchangers and condensers. The reference electrode includes a bolt, one or more elastomer cylinders placed over the bolt and flanked by stress distribution washers on both ends, and a non-metallic housing containing the reference electrode element and having an internal thread at one end matching the thread on the compression bolt. This assembly is inserted into a tube on the tube sheet, only the housing containing the reference electrode element is exposed. The housing may be rotated to cause the elastomer cylinders to expand and lock against the inside wall of the tube.

23 Claims, 4 Drawing Sheets

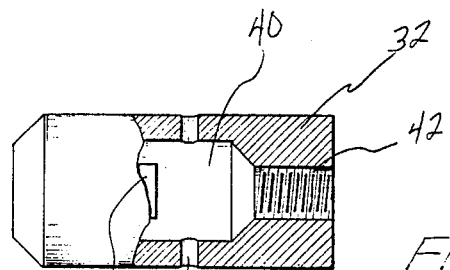
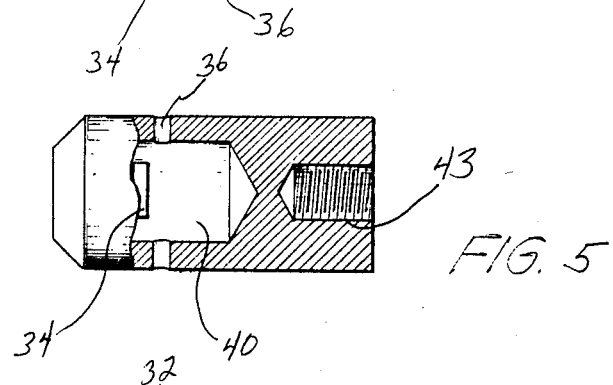
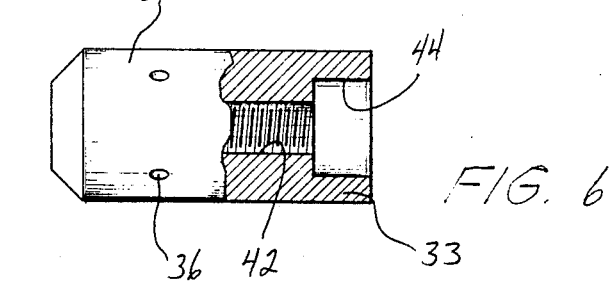

4,957,616

TUBE SHEET WITH REFERENCE ELECTRODE

This is a continuation of SN 277,490, filed Nov. 29, 1988, which is a continuation of SN 030,876, filed Mar. 26, 1987, abandoned.

BACKGROUND OF THE INVENTION

The present invention relates to a reference electrode and more particularly to a reference electrode apparatus for use in connection with a tube sheet for a condenser or heat exchanger.

Condensers and heat exchangers used for power plants and in the oil refining industry include large tube sheets into which tubes are inserted. As these condensers and heat exchangers are used in environments in which metallic parts can corrode, it is a constant goal to prevent such corrosion and thereby extend the life of the tubes and tube sheets.

One means of preventing corrosion of metallic parts immersed in a corrosive electrolyte, such as seawater, is through cathodic protection which utilizes an electric current flowing between an anode and the surface to be protected which is the cathode. The current may be generated naturally by using an anode, commonly referred to as a sacrificial anode, which is more electronegative than the cathode. Alternatively, the current may be supplied by an electrical device commonly referred to as an Impressed Current Cathodic Protection System. If an excess of current flows between the anode and cathode, hydrogen can be generated at the cathode which can embrittle certain susceptible metals, such as titanium or ferritic stainless steels, or cause the blistering of any paint films which have been applied to the surface. On the other hand, if an insufficient amount of current is applied, the surface will not be fully protected against corrosion. Therefore, an optimum level of protection current exists, and this optimum level can be determined by measuring the potential of the protected surface as this surface will establish a certain optimum potential when the proper level of protection current has been applied. Overprotected surfaces will be more negative and underprotected surfaces less negative than the optimum protection potential.

In order to measure the potential of the protected surface, reference electrodes are immersed in the electrolyte and the potential between the reference electrode and the protected surface is measured with an electrometer or other similar instrument. This measurement can then be used to control the current by manually or automatically adjusting the protection current level to keep this potential as close to the optimum as practical. Reference electrodes used for this purpose include: silver/silver chloride, calomel, zinc and copper/copper sulphate, in addition to other types.

A reference electrode should be positioned as close to the surface to be measured as practical. Increasing the distance between the reference electrode and the surface to be measured decreases the accuracy of the measurement by providing interference from the resistance of the electrolyte as well as by masking local variations in potential which can be indicative of areas of the cathode which are being under or over protected. While minimizing the distance between the reference electrode and the cathode surface is possible in laboratory environments, it has not been practical to do so in industrial applications such as shell and tube heat exchangers and condensers.

In the case of a cathodically protected tube sheet 12 shown in FIG. 1, the reference electrode 16 will frequently be mounted on the wall of a water box 18 and located several feet away from the surface of the tube sheet 12. A principal reason why electrodes are positioned several feet from the surface of the tube sheet is that there is no simple and reliable way to permanently and rigidly mount a reference electrode directly on the surface of the tube sheet.

It is therefore a principal object of the present invention to provide a reference electrode for use in conjunction with a tube sheet for a shell and tube heat exchanger or condenser.

It is a further object of the present invention to provide a reference electrode which may be positioned in close proximity to a tube sheet for a tube heat exchanger or condenser.

Still another object of the present invention is to provide a reference electrode that can be mounted to tube plugs already inserted in an end of a tube inserted to a tube sheet.

Yet another object of the present invention is to provide a reference electrode that can be permanently and rigidly mounted on the surface of the tube sheet.

SUMMARY OF THE INVENTION

A tube sheet with an attached reference electrode is provided for use in heat exchangers and condensers. In a preferred embodiment, the reference electrode includes a bolt, one or more elastomer cylinders placed over the bolt and flanked by stress distribution washers on both ends, and a non-metallic housing containing the reference electrode element and having an internal thread at one end matching the thread on the compression bolt. This assembly is inserted into a tube in a tube sheet so that only the housing containing the reference electrode element is exposed. The housing may be rotated to cause the elastomer cylinders to expand and lock against the inside wall of the tube.

These and other objects and features of the present invention will be more fully understood from the following detailed description which should be read in light of the accompanying drawings in which corresponding reference numerals refer to corresponding parts throughout the several views.

BRIEF DESCRIPTION OF THE DRAWING

FIG. 4 is a cross-sectional view of a portion of the tube sheet reference electrode shown in FIG. 3;

FIG. 5 is a cross-sectional view of an alternate embodiment of the tube sheet reference electrode shown in FIG. 3;

FIG. 6 is a side elevational view, partly in section, of a further alternate embodiment of the tube sheet reference electrode shown in FIG. 3;

FIG. 11 is a plan view of a heat exchanger or condenser using the tube sheet with reference electrode of the present invention.

DESCRIPTION OF THE PREFERRED EMBODIMENT

Figure 2A:
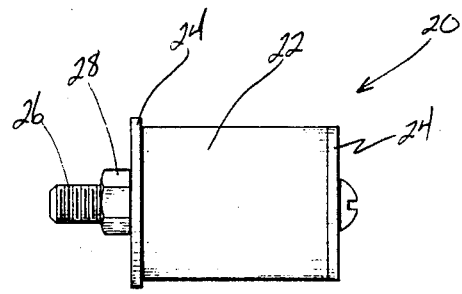
FIG. 2a is a side elevational view of a known single compression-type tube plug.

Referring to FIG. 2a, a known single compression-type tube plug 20 is shown which includes an elastomer cylinder 22 flanked on both ends by stress distribution washers 24. A compression bolt 26 passes through the center of the cylinder 22 and the washers 24 and engages a compression nut 28. The diameter of the cylinder 22 is approximately the same as the inside diameter of the tube for which it is designed.

Figure 1:
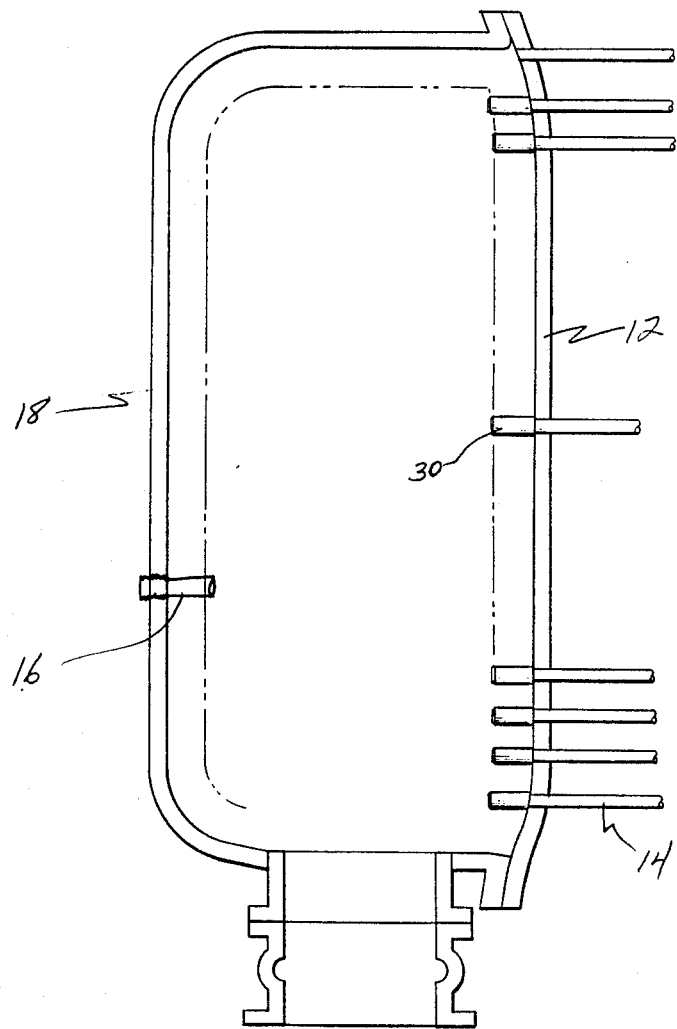
FIG. 1 is a plan view of a shell and tube heat exchanger and condenser tube sheet.

In use, the plug 20 is inserted into a tube 14 (FIG. 1) and the nut 28 is tightened. The tightening of the nut 28 draws the washers 24 together reducing the length of the cylinder 22 while causing the diameter of the elastomer cylinder 22 to expand and thereby create a tight seal against the inner wall 15 of the tube 14. The primary purpose of this device is to seal the end of a tube.

Figure 2B:
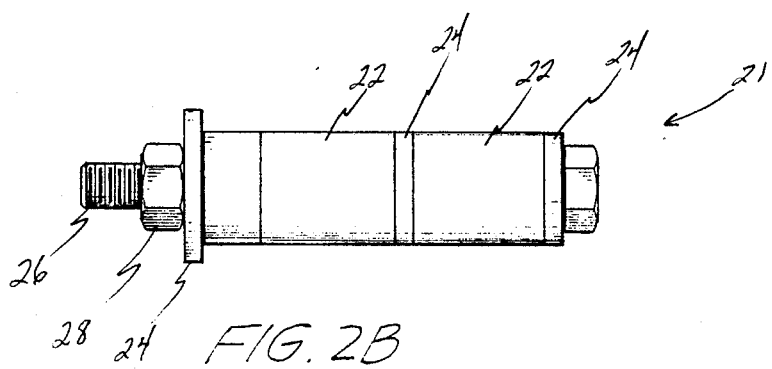
FIG. 2b is a side elevational view of a known double compression-type tube plug.

Referring now to FIG. 2b, there is shown a double compression-type tube plug 21 which includes two elastomer cylinders 22, stress distribution washers 24 on each end of the plug, and an intermediate washer 24 positioned between the two cylinders 22. Such double tube plugs 21 are used where greater sealing area between the cylinders and the tube wall is required.

The bolts utilized in either type of compression plug may be metallic or non-metallic bolts depending upon the application, and either the single, double or other equivalent models can be incorporated into the present invention.

Figure 3:
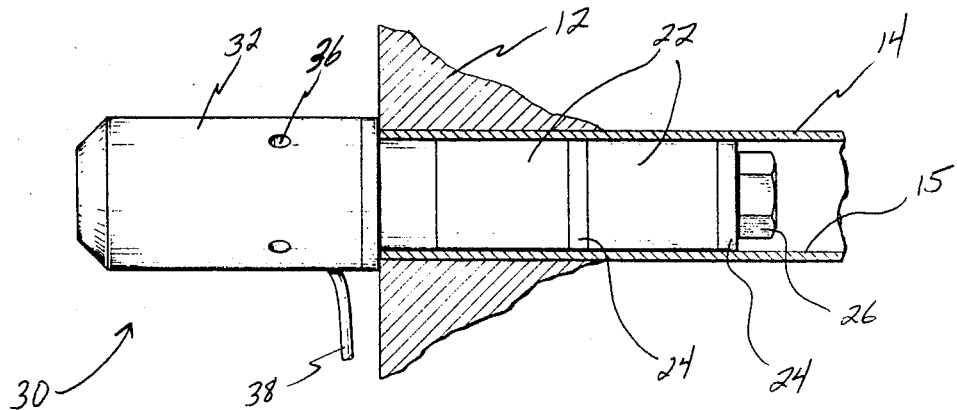
FIG. 3 is a side elevational view, partly in section, of the tube sheet with reference electrode of the present invention.

FIG. 3 shows the tube sheet reference electrode 30 mounted to a double tube plug 21 inserted in a tube 14. The reference electrode includes a non-metallic housing 32 surrounding the reference electrode element 34 (see FIGS. 4 and 5). The housing 32 may be mounted over a compression nut 28 or it may take the place of the compression nut in forcing the washers 24 together to expand the cylinders 22. When the housing 32 is mounted over the compression nut 28, it may be designed to fit snugly over the nut 28 so that rotation of the housing causes rotation of the nut 28, or the housing 32 may fit loosely over the nut 28 so that rotation of the housing 32 does not result in rotation of the nut.

The electrode element may be silver/silver chloride (and may be immersed in a constant chloride gel), calomel, copper/copper sulfate, zinc as well as other known materials. The housing also includes several holes 36 through the housing 32 that allow the electrolyte to flow into the housing and contact the reference electrode element. A lead wire 38 is cemented to the face of the tube sheet 12 and routed to a location where it can be passed through a waterproof throughwall gland to the exterior of the connector where it is accessible for measurements. While several types of wire insulation can be used, a Teflon-type insulation is preferred due to its high resistance to water permeation, heat and abrasion.

The housing 32, shown in greater detail in FIG. 4, includes an internal threaded opening 42. This housing 32 connects to a plug having a non-metallic compression bolt 26, and the threaded hole can extend entirely through the housing wall into the internal chamber 40 containing the sensing element 34 because when the housing is installed, the bolt 26 will close off the opening.

In FIG. 5, an alternate embodiment of the housing 32 is shown which is designed principally for use with a metallic compression bolt 26. With this reference electrode device, a threaded hole 43 does not communicate directly with the internal chamber 40. It is possible to design this housing so that there is communication directly with the internal chamber, but the chamber must somehow be plugged at the internal end because the presence of the metallic bolt so close to the sensing element could give erroneous measurements.

A further alternate embodiment to the reference electrode shown in FIG. 6 is designed for use on a tube plug in which the compression nut 28 has already been installed. A cylindrical chamber 44 provided in the housing 32 is of a diameter and depth slightly greater than the diameter and height of the nut 28. When installed, the annular face 33 of the housing should bear against the outer compression washer 24 of the tube plug thereby providing a good seating.

Figure 7:
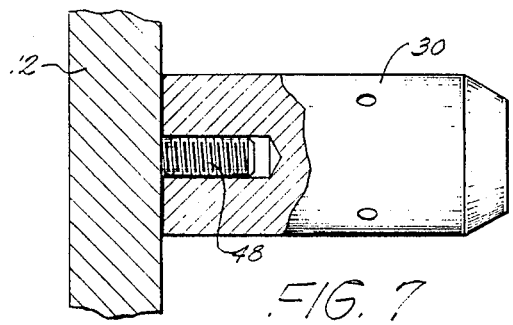
FIGS. 7–10 are views of additional alternate embodiments of the tube sheet reference electrode shown in FIG. 3.
Figure 8:
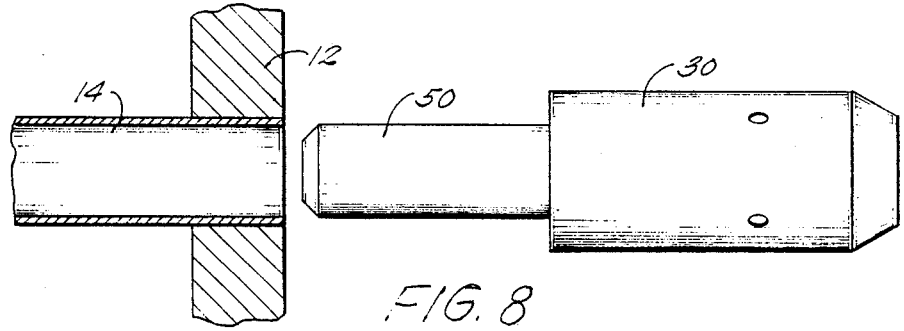
Figure 9:
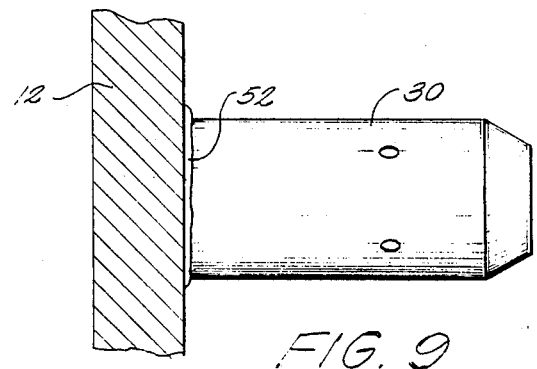
Figure 10:
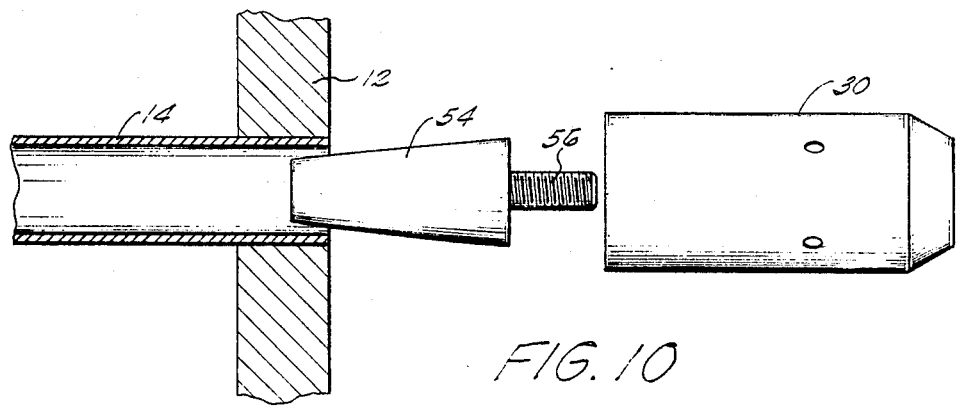

Referring to FIG. 7, there is shown a threaded stud 48 which is welded, tapped or threaded to a face of the tube sheet 12. The reference electrode 30 is then threaded onto the stud 48. In the embodiment shown in FIG. 8, the threaded end of the housing 30 is replaced with a cylinder 50 sized to slip into the tube with the cylinder 50 being cemented in place. Also, as shown in FIG. 9, the housing 30 should be directly cemented with a layer of cement 52 to the tube sheet 12, or as shown in FIG. 10, the compression plug could be replaced by a tapered plug 54 which is affixed to a threaded stud 56 for attaching the reference electrode 30. FIG. 11 shows a heat exchanger or condenser using the tube sheet with reference electrode 30 of the present invention.

EXAMPLE

The following non-limiting example is one of many possible configurations of the tube sheet with reference electrode apparatus of this invention.

Fourteen tube sheet mounted silver/silver chloride reference electrodes, of the type shown in FIG. 3, were installed on each of the main condenser inlet and outlet tube sheets at a large electrical generating station. The specific locations of the reference electrodes were chosen so that some were positioned close to the anodes, while others were positioned remote from the anodes. The tubes were made of titanium while the tube sheet was made of an aluminum bronze alloy coated on the inlet to provide partial protection from the corrosive effects of the sea water contained therein. A cathodic protection system had been installed to provide supplementary protection. The single silver/silver chloride reference electrode previously installed on the wall of the water box indicated a tube sheet potential of −0.900 volts which is considered within the optimum range for these materials, and there had been no history of tube failures due to hydrogen damage at this particular unit.

When potential measurements were made with the tube sheet mounted reference electrodes of the present invention, the results were quite unexpected. Instead of the entire tube sheet being at a uniform potential of −0.900 volts, these measurements show that the actual potential varied over a range of 0.460 volts across the face of the tube sheet. Specifically, the tube sheet potential varied from a low of −0.790 volts at a location remote from an anode, which is barely adequate protect the bronze tube sheet, to a high of −1.250 volts at a location close to an anode which is considered excessive for titanium and capable of causing hydrogen damage. Subsequent metallurgical examination of tubes located at the highly electronegative sites demonstrated that incipient hydrogen embrittlement had begun. While the condition was still a long way from the point of causing failure, if corrective action had not been taken, the tubes would have ultimately failed.

While the foregoing invention has been described with reference to its preferred embodiments, various alterations and modifications will occur to those skilled in the art. All such alterations and modifications are intended to fall within the scope of the appended claims.

What is claimed is:

1. A tube sheet for a shell and tube heat exchanger or condenser, comprising:
   a perforated sheet having a waterbox side and a shell side;
   a plurality of tubes each having an inside diameter, wherein said tubes are inserted through the perforations in said perforated sheet and extend on the shell side of said perforated sheet; and
   a reference electrode apparatus adapted to be installed from the waterbox side of the perforated sheet for use on the waterbox side of said perforated sheet, including
      means plugging one of said plurality of tubes at the end of said tube located proximal to said perforated sheet, said plugging means including a sealing means positioned within said tube and having an outer diameter approximately equal to the inside diameter of said tube, and a connecting means extending from said tube,
      a reference electrode attached to said connecting means, said reference electrode including means for referencing electrical potential measurements, a housing surrounding said referencing means, and means securing said housing to said connecting means, and
      a lead wire extending from said reference electrode on the waterbox side of said perforated tube sheet.

2. The tube sheet of claim 1 wherein said plugging means comprises a single tube plug including:
   an elastomer cylinder;
   a stress distribution washer placed on each end of said cylinder;
   a compression bolt extending through said cylinder and said stress distribution washers with a compression nut mounted on one end of said compression bolt.

3. The tube sheet of claim 2 wherein said compression bolt is a metallic compression bolt.

4. The tube sheet of claim 2 wherein said compression bolt is a non-metallic compression bolt.

5. The tube sheet of claim 2 wherein said housing further comprises a recess for receiving said compression nut.

6. The tube sheet of claim 1 wherein said means for referencing electrical potential measurements is a silver/silver chloride electrode.

7. The tube sheet of claim 6 wherein said means for referencing electrical potential measurements is immersed in a constant chloride electrolyte.

8. The tube sheet of claim 1 wherein said means for referencing electrical potential measurements is a calomel electrode.

9. The tube sheet of claim 1 wherein said means for referencing electrical potential measurements is a copper/copper sulfate electrode.

10. The tube sheet of claim 1 wherein said means for referencing electrical potential measurements is a zinc electrode.

11. The tube sheet of claim 1 wherein said plugging means comprises a double tube plug including:
    two elastomer cylinders,
    stress distribution washer placed on each end of said cylinders and between said two elastomer cylinders,
    a compression bolt extending through said cylinders and said washers with a compression nut mounted on one end of said compression bolt.

12. The tube sheet of claim 11 wherein said compression bolt is a metallic bolt.

13. The tube sheet of claim 11 wherein said compression bolt is a non-metallic bolt.

14. The tube sheet of claim 1 wherein said housing includes an internal threaded portion threadably engaging said connecting means.

15. The tube sheet of claim 1 wherein said housing includes an internal threaded portion threadably engaging said connecting means and includes an internal chamber surrounding said means for referencing electrical potential measurements, said chamber including means for communicating with the ambient environment surrounding said housing.

16. The tube sheet of claim 15 wherein said internal chamber is in communication with said internal threaded portion.

17. The tube sheet of claim 15 wherein said means for communicating with the ambient environment comprises holes through a wall of said housing.

18. A tube sheet for a shell and tube heat exchanger or condenser, comprising:
    a perforated sheet having a waterbox side and a shell side;
    a plurality of tubes, wherein said tubes are inserted through perforations in said sheet and extend on the shell side of said perforated sheet; and
    a reference electrode apparatus for use on the water box side of said perforated sheet, including
       a reference electrode mounted on the tube sheet on the waterbox side of said tube sheet, said reference electrode including means for referencing electrical potential measurements, a housing surrounding said referencing means, means for allowing a flow of electrolyte to contact said referencing means, means extending into one of said tubes at an end located proximal to said perforated sheet, and means securing said housing to said perforated tube sheet, and
       a lead wire extending from said reference electrode on the waterbox side of said perforated tube sheet.

19. The tube sheet of claim 18 wherein said extending means has the shape of a cylinder with an external circumference substantially matching the internal circumference of the tube into which said cylinder extends.

20. The tube sheet of claim 18 wherein said securing means comprises cementing means.

21. A shell and tube heat exchanger, comprising:
    a pressure vessel;
    two tube sheets for creating a shell compartment and two waterbox compartments within said pressure vessel, wherein each of said two tube sheet comprises
- a perforated sheet having a waterbox side and a shell side, and
- a plurality of tubes, wherein said tubes are inserted through perforations in said perforated sheet and extend on the shell side of said perforated sheet; and
- a reference electrode apparatus adapted to be installed from the waterbox side of said perforated sheet for use on the waterbox side of said perforated sheet, comprising
  - means plugging one of said plurality of tubes at an end of said tube, said plugging means including a sealing means positioned within said tube and having an outer diameter approximately equal to the inside diameter of said tube, and a connecting means extending from said tube,
  - a reference electrode attached to said connecting means, said reference electrode including means for referencing electrical potential measurements, a housing surrounding said referencing means, and means securing said housing to said connecting means, and
  - a lead wire extending from said reference electrode on the waterbox side of said perforated sheet.

22. A shell and tube condenser, comprising:
a pressure vessel;
two tube sheets for creating a shell compartment and two waterbox compartment within said pressure vessel, wherein each of said two tube sheets comprises;
- a perforated sheet having a waterbox side and a shell side, and
- a plurality of tubes, wherein said tubes are inserted through perforations in said perforated sheet and extend on the shell side of said perforated sheet; and
- a reference electrode apparatus adapted to be inserted from the waterbox side of said perforated sheet for use on the waterbox side of said perforated sheet, comprising
  - means plugging one of said plurality of tubes at an end of said tube, said plugging means including a sealing means positioned within said tube and having an outer diameter approximately equal to the inside diameter of said tube, and a connecting means extending from said tube,
  - a reference electrode attached to said connecting means, said reference electrode including means for referencing electrical potential measurements, a housing surrounding said referencing means, and means securing said housing to said connecting means, and
  - a lead wire extending from said reference electrode on the waterbox side of said perforated sheet.

23. A tube sheet for use with shell and tube heat exchanger and condenser tube sheets comprising:
- a tapered pin plug driven into a tube inserted in the tube sheet, said tapered pin plug including a threaded extension;
- a reference electrode, said reference electrode including means for referencing electrical potential measurements, a housing surrounding said means for referencing electrical potential measurements, and means for allowing a flow of electrolyte to contact said means for referencing electrical potential measurements; and
- an internally threaded opening in said housing threadably connecting said housing to said threaded extension.

* * * * *